(12) United States Patent
Millerd

(10) Patent No.: US 7,357,783 B2
(45) Date of Patent: Apr. 15, 2008

(54) SAFETY SYSTEM FOR A BLOOD COLLECTION DEVICE

(75) Inventor: Don Millerd, San Diego, CA (US)

(73) Assignee: MedPro Safety Products, Inc., Lexington, KY (US)

( * ) Notice: Subject to any disclaimer, the term of this patent is extended or adjusted under 35 U.S.C. 154(b) by 140 days.

(21) Appl. No.: 10/621,973

(22) Filed: Jul. 17, 2003

(65) Prior Publication Data

US 2005/0015058 A1 Jan. 20, 2005

(51) Int. Cl.
*A61M 5/00* (2006.01)
(52) U.S. Cl. .................................................... 604/110
(58) Field of Classification Search .............. 604/110, 604/198, 192, 137, 263, 167.8, 187
See application file for complete search history.

(56) References Cited

U.S. PATENT DOCUMENTS

| | | | |
|---|---|---|---|
| 4,631,057 A | 12/1986 | Mitchell | |
| 4,725,267 A | 2/1988 | Vaillancourt | |
| 4,813,940 A | 3/1989 | Parry | |
| 4,842,587 A | 6/1989 | Poncy | |
| 4,892,107 A | 1/1990 | Haber | |
| 4,894,055 A | 1/1990 | Sudnak | |
| 4,923,447 A | 5/1990 | Morgan | |
| 5,049,133 A | 9/1991 | Villen Pascual | |
| 5,049,136 A | 9/1991 | Johnson | |
| 5,092,851 A | 3/1992 | Ragner | |
| 5,267,977 A | 12/1993 | Feeney, Jr. | |
| 5,292,314 A | 3/1994 | D'Alessio et al. | |
| 5,346,480 A | 9/1994 | Hess et al. | |
| 5,389,085 A | 2/1995 | D'Alessio et al. | |
| 5,403,286 A | 4/1995 | Lockwood, Jr. | |
| 5,478,316 A | 12/1995 | Bitdinger et al. | |
| 5,582,597 A | 12/1996 | Brimhall et al. | |
| 5,688,241 A | 11/1997 | Asbaghi | |
| 5,695,475 A | 12/1997 | Best, Jr. et al. | |
| 6,186,980 B1 | 2/2001 | Brunel | |
| 6,190,361 B1 | 2/2001 | Gettig et al. | |
| 6,203,529 B1 * | 3/2001 | Gabriel et al. | 604/192 |
| 6,379,336 B1 | 4/2002 | Asbaghi et al. | |
| 6,623,458 B2 | 9/2003 | Woehr et al. | |
| 6,641,555 B1 * | 11/2003 | Botich et al. | 604/110 |
| 6,761,706 B2 | 7/2004 | Vaillancourt | |
| 6,860,871 B2 | 3/2005 | Kuracina et al. | |
| 6,869,415 B2 * | 3/2005 | Asbaghi | 604/110 |
| 2001/0044607 A1 * | 11/2001 | DeMichele et al. | 604/192 |

* cited by examiner

*Primary Examiner*—Kevin C. Sirmons
*Assistant Examiner*—Catherine N. Witczak
(74) *Attorney, Agent, or Firm*—Frost Brown Todd LLC

(57) ABSTRACT

A system includes a needle for aspirating fluid. A holder supports the needle and a guard is moveable to selectively cover the needle. Initially, a cantilevered tab on the guard is moved into a stressed configuration, and a distally directed force on the guard presses the tab into contact with an abutment on the holder. This prevents further distal movement of the guard. Subsequently, in response to a proximally directed force, the tab is released from the abutment, it returns to a passive, unstressed configuration, and the guard moves to expose the needle for aspiration. Thereafter, when the proximally directed force on the guard is removed, the guard is urged into a final, locked position where it covers the distal end of the needle and protects the needle.

11 Claims, 2 Drawing Sheets

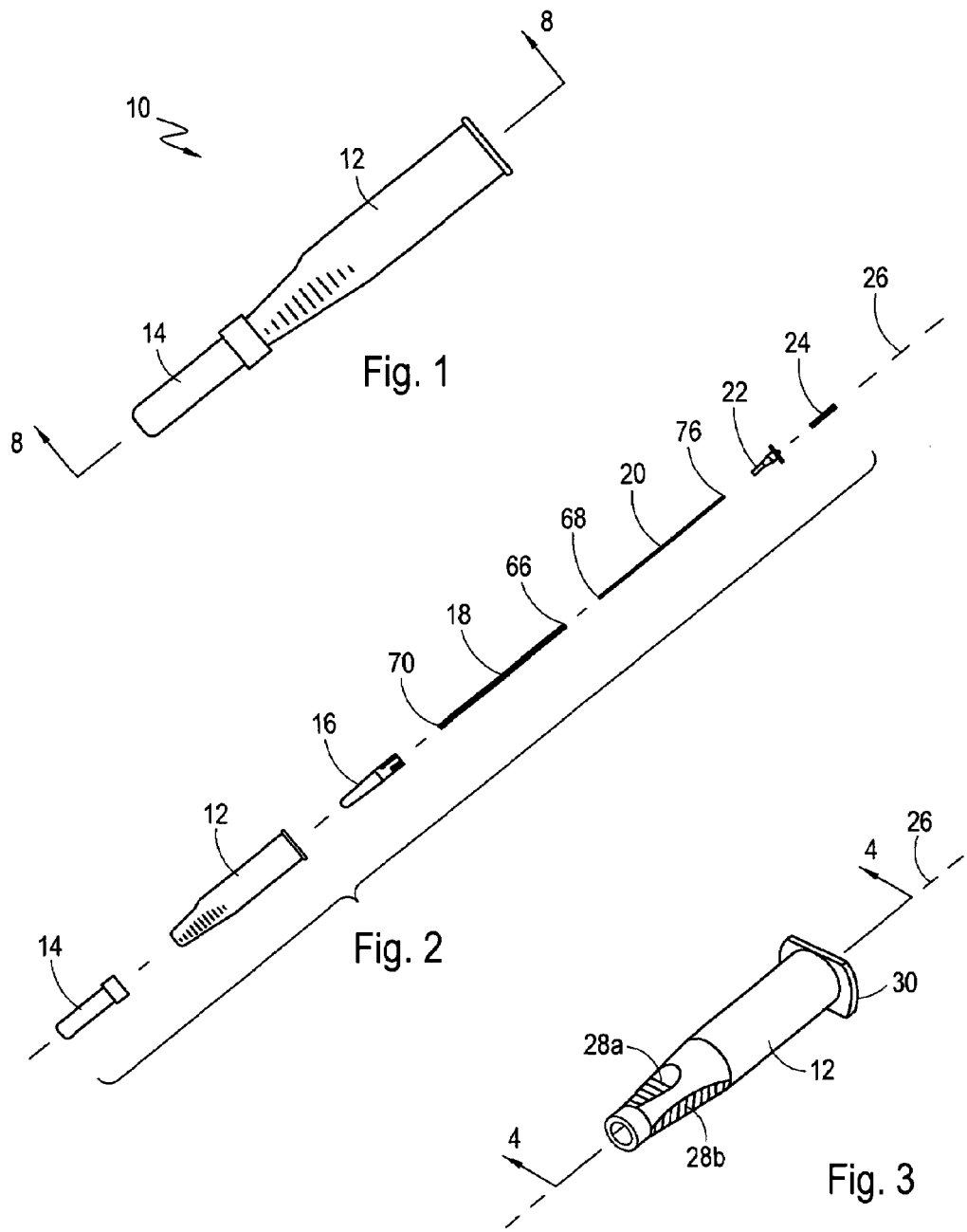

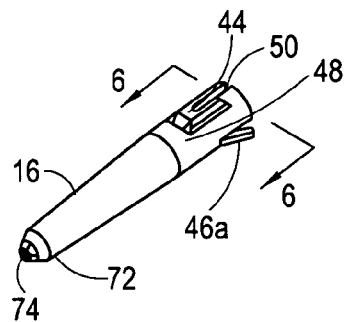
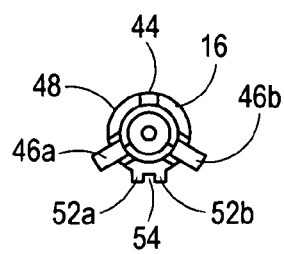
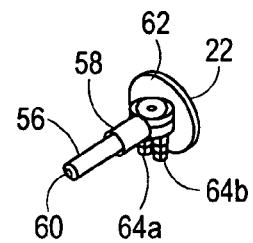
Fig. 5  Fig. 6  Fig. 7
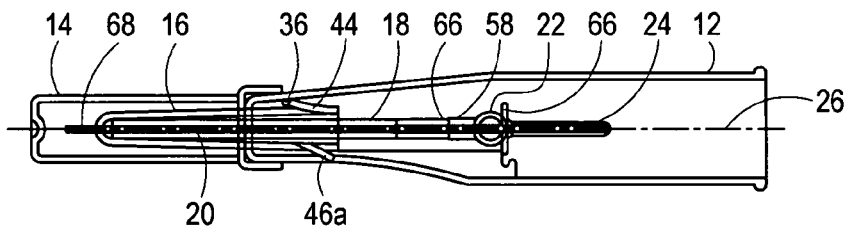
Fig. 8A
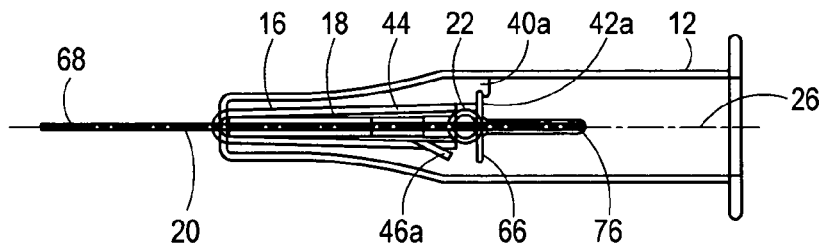
Fig. 8B
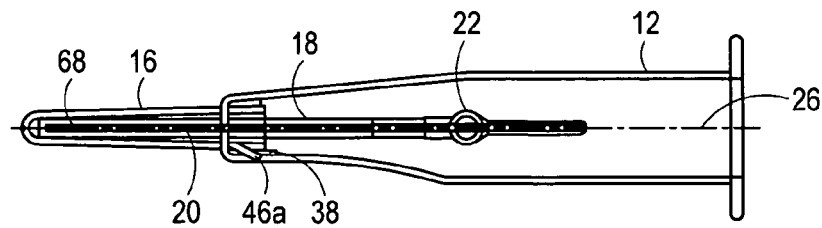
Fig. 8C

SAFETY SYSTEM FOR A BLOOD COLLECTION DEVICE

FIELD OF THE INVENTION

The present invention pertains generally to fluid collection systems. More particularly, the present invention pertains to fluid aspiration systems that are useful for collecting blood. The present invention is particularly, but not exclusively, useful as a blood collection system having an automatically activated guard that covers the needle to protect users from accidental "sticks" after blood has been collected.

BACKGROUND OF THE INVENTION

Any use of a needle requires careful handling and the exercise of caution. The main purpose for this, of course, is to protect against inadvertent "sticks" that can cause injury and may transmit diseases. Such care is particularly important when the needle is a hypodermic needle and is being used as an injection or aspiration needle in blood transfer, or blood collection procedures. In addition to careful handling of a needle, the safety of a needle procedure can be enhanced if the needle can be effectively covered whenever it is not being used.

Heretofore, several different types of safety systems have been disclosed which are designed for both ease of use and protection of the user. Typically, these systems incorporate automatic features that help minimize the manipulation required to effectively use a needle in a procedure. For example, U.S. Pat. No. 6,379,336 which issued to Asbaghi et al. for an invention entitled "Protective Device for Injection or Aspiration Needle", and which is assigned to the same assignee as the present invention, discloses a system that automatically locks a guard over a needle after its use.

For the specific application wherein a needle system is used for blood collection, there is no need for the needle system to be somehow prepared before it is to be used. For instance, in a blood collection procedure there is no need to pre-fill a syringe with medication, or to otherwise uncover and prepare the needle prior to its use. Consequently, an aspiration needle is preferably ready for use at any time. After its use, however, when there is no longer a need for the needle, it is desirable for the needle to be permanently covered to protect the user, and others, from accidental sticks.

In light of the above, it is an object of the present invention to provide a safety system for a blood collection device that has an automatic, ready-to-activate, needle guard for covering and protecting the needle after its use. Another object of the present invention is to provide a safety system for a blood collection device that automatically locks the needle guard in place after the needle has been used. Yet another object of the present invention is to provide a safety system for a blood collection device that is simple to manufacture, is easy to use and is comparatively cost effective.

SUMMARY OF THE INVENTION

In accordance with the present invention, a safety system for a blood collection device includes a tubular shaped holder and a tubular shaped guard. The holder and guard then interact with each other to protect the needle of the device after it has been used. Structurally, the holder defines a longitudinal axis, and it has an inner surface that surrounds a lumen. A distal abutment and a proximal abutment are formed on the inner surface of the holder, along with a plurality of longitudinally oriented ribs. More specifically, the ribs individually extend from the inner surface of the holder and each rib is formed with a detent. Using this arrangement, the needle is mounted on an adapter, and the adapter is affixed to the ribs by a snap engagement with the respective detents. This aligns the needle along the axis of the holder.

For their interaction with each other, the guard is positioned inside the lumen of the holder with its outer surface facing the inner surface of the holder. Also, a spring is positioned between the guard and the adapter to urge the guard in a distal direction along the axis. Importantly, the guard is formed with a cantilevered tab that can be outwardly deflected from the surface of the guard, into a stressed configuration. With the cantilevered tab in this stressed configuration, the spring urges the tab against the distal abutment on the holder to prevent further movement of the guard in a distal direction. This puts the guard in a ready-to-activate condition. On the other hand, when the tab is lifted from the distal abutment it will move from its stressed configuration, into an unstressed configuration. In this unstressed configuration, the cantilevered tab is flush with the outer surface of the guard and is clear of any interaction with the holder.

In the operation of the system of the present invention, the guard is sequentially moved through three, distinctly identifiable positions. These are an initial position, a retracted position, and a final (locked) position. In its initial position (i.e. the ready-to-activate condition discussed above) the cantilevered tab on the guard is in its stressed configuration. Also, the tab is being urged against the distal abutment to hold the guard stationary, relative to the holder. In this initial position, a distal portion of the needle extends from the guard. A cover can be engaged with the holder to protect the exposed distal end of the needle.

For use of the system in a blood collection procedure, the cover is removed from the holder. The needle is then inserted to establish fluid communication with a patient (fluid source). With this insertion, the guard is moved over the needle in the proximal direction to the retracted position. This causes further exposure of the needle and causes the cantilevered tab to be lifted from the distal abutment. The cantilevered tab then transitions into its unstressed configuration.

Upon completion of the blood collection procedure, the needle is withdrawn and the guard moves in the distal direction to its final position. In this final position, the guard covers the distal portion of the needle, and an extension limiter that is formed on the guard is engaged with the proximal abutment to prevent an uncovering of the distal portion of the needle.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which:

FIG. 1 is a perspective view of the safety system for a fluid collection device in accordance with the present invention;

FIG. 2 is an exploded view of the system showing the interrelationship of its constituent components;

FIG. 3 is a perspective view of the holder;

FIG. 4 is a cross-sectional view of the holder as seen along the line 4-4 in FIG. 3;

FIG. 5 is a perspective view of the guard;

FIG. 6 is an end view of the guard as seen along the line 6-6 in FIG. 5;

FIG. 7 is a perspective view of the adapter;

FIG. 8A is a cross-sectional view of the system as seen along the line 8-8 in FIG. 1 with the guard in its initial position;

FIG. 8B is a cross-sectional view of the system as seen along the line 8-8 in FIG. 1 with the guard in its retracted position; and FIG. 8C is a cross-sectional view of the system as seen along the line 8-8 in FIG. 1 with the guard in its final, locked position.

DESCRIPTION OF THE PREFERRED EMBODIMENTS

Referring initially to FIG. 1, a safety system for a blood collection device is shown and generally designated 10. As shown, the system 10 includes a holder 12 and a cover 14 that is engageable with the holder 12. In addition to the holder 12 and cover 14, all of the various components of the system 10, and their interrelationship with each other are, perhaps, best seen with reference to FIG. 2.

In FIG. 2, the system 10 is shown to include a guard 16, a spring 18, a needle 20, and an adapter 22, as well as a sheath 24. These components are shown aligned along an axis 26, with the cover 14 being shown in a distal position, and the sheath 24 being shown in a proximal position.

Details of the holder 12 will be best appreciated with reference to both FIG. 3 and FIG. 4. FIG. 3 shows that the holder 12 is externally formed with finger grips 28 (the grips 28a and 28b are exemplary), and a base flange 30. In more detail FIG. 4 shows that the holder 12 is substantially tubular in shape and that, internally, it has an inner surface 32 that surrounds a lumen 34. Further, it is seen that the inner surface 32 is formed with a distal abutment 36, and at least one proximal abutment 38. Still further, it is seen that the inner surface 32 of holder 12 is formed with ribs 40 (the ribs 40a and 40b are exemplary) that extend longitudinally in the lumen 34 of holder 12, substantially parallel to the axis 26. Also, all of the ribs 40 (e.g. ribs 40a and 40b) are shown formed with a respective detent 42 (e.g. detents 42a and 42b).

The guard 16 is best understood with reference to both FIG. 5 and FIG. 6. Specifically, FIG. 5 shows that the guard 16 is formed with a cantilevered tab 44 and a pair of extension limiters 46a and 46b (also see FIG. 6). More specifically, the cantilevered tab 44 is shown flush with the outer surface 48 of the guard 16 in FIG. 5. In this configuration (i.e. when the tab 44 is flush with the outer surface 48) the cantilevered tab 44 is unstressed. It is to be appreciated, however, that when the cantilevered tab 44 is deflected outwardly from the outer surface 48 of the guard 16, it is placed in a stressed configuration. In this stressed configuration, the cantilevered tab 44 will be biased to return to its unstressed configuration. FIG. 5 also shows the cantilevered tab 44 is formed with a channel 50. Specifically, the channel 50 is provided so that a tool (not shown) can be inserted into the channel 50 from the proximal end of the guard 16 to deflect the cantilevered tab 44 into its stressed configuration during assembly of the system 10. Additionally, FIG. 6 shows that the guard 16 is formed with a pair of ridges 52a and 52b that form a groove 54.

FIG. 7 shows that the adapter 22 includes an extension 56 that is formed with a shoulder 58. This extension 56 of adapter 22 is formed with a lumen 60 and, additionally, the adapter 22 includes a disk 62 that is oriented substantially perpendicular to the extension 56. Further, the adapter 22 has a pair of parallel prongs 64a and 64b that are substantially perpendicular to the extension 56.

In the assembly of the system 10, the needle 20 is positioned through the lumen 60 of adapter 22 and is held on the adapter 22 by means well known in the pertinent art, such as by solvent bonding. The spring 18 is then placed over the distal end (portion) 68 of the needle 20, and also over the extension 56 of the adapter 22. This positions the proximal end 66 of spring 18 against the shoulder 58. The distal end (portion) 68 of needle 20, and the distal end 70 of spring 18 are then inserted into the guard 16. With this insertion, the distal end 70 of spring 18 is positioned against the distal end 72 of the guard 16, and the distal end (portion) 68 of needle 20 can extend through the opening 74 at the distal end 72 of guard 16. This combination is then engaged with the holder 12.

For engagement of the guard 16 with the holder 12, a tool (not shown) is forced into the channel 50 of cantilevered tab 44 to deflect the cantilevered tab 44 into its stressed configuration. The guard 16 is then inserted into the lumen 34 of holder 12. During this insertion, the guard 16 is positioned so that one of the ribs 40 (e.g. rib 40b) is received in the groove 54 created by the ridges 52a and 52b. This interaction then prevents a rotation of the guard 16 relative to the holder 12. Also, during this insertion, the prongs 64a and 64b on adapter 22 are positioned to also straddle one of the ribs 40. With these components oriented in this manner, insertion continues until the disk 62 of adapter 22 snaps into engagement with the detents 42 of ribs 40.

With the snap engagement of adapter 22 with the detents 42 on ribs 40, the cantilevered tab 44 (now in its stressed configuration) is forced by the compressed spring 18 into contact with the distal abutment 36. Specifically, as long as there is no proximally directed force on the guard 16, the distally directed force of spring 18 will hold the cantilevered tab 44 against the distal abutment 36, in its stressed configuration. The cover 14 is then engaged with the holder 12 to protect the otherwise exposed distal end (portion) 68 of the needle 20. This places the guard 16 in an initial position where it is in a ready-to-activate condition (see FIG. 8A).

In the operation of the system 10 of the present invention, the cover 14 is first removed. As seen in FIG. 8A, this will expose the distal end (portion) 68 of needle 20 so it can be inserted into a patient (not shown) and used for a blood collection procedure. As the needle 20 is being inserted into the patient, a force is generated against the compression force in spring 18. This causes the guard 16 to move in the proximal direction along axis 26 to a retracted position (shown in FIG. 8B). As the guard 16 moves to this retracted position, the cantilevered tab 44 is lifted from the distal abutment 36. This then allows the cantilevered tab 44 to return to its unstressed configuration. Importantly, in its unstressed configuration, the cantilevered tab 44 is now flush with the outer surface 48 of guard 16 and clear of any subsequent interaction with the holder 12.

While the guard 16 is in its retracted position (FIG. 8B), a fluid collection vial (not shown) can be connected in fluid communication with the proximal end 76 of needle 20. As will be appreciated by the skilled artisan, sequential fluid collection vials can be so connected. Then, after the fluid collection procedure is completed, the needle 20 can be withdrawn from the patient. With this withdrawal, the compression force in spring 18 causes the guard 16 to move in a distal direction along the axis 26 to move the guard 16 into its final (locked) position (FIG. 8C). In this final position, the ridges 52a and 52b on guard 16 are in contact with the holder 12 to prevent any additional movement of the guard 16 in a distal direction on the holder 12. Also, in this final position, the extension limiters 46a and 46b on the guard 16 are engaged, respectively, with a proximal abutment 38 to prevent any additional movement of the guard 16 in a proximal direction on the holder 12. Thus, the guard 16 is locked to cover the distal end (portion) 68 of needle 20 to protect the user from an inadvertent "stick" by the needle 20. The system 10 can then be discarded.

While the particular safety system for a blood collection device as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A protective device for a needle which comprises:
   a substantially tubular shaped holder defining a longitudinal axis and having an inner surface surrounding a lumen;
   a distal abutment formed on the inner surface of the holder;
   a proximal abutment formed on the inner surface of the holder;
   an adapter with the needle mounted thereon, the adapter being affixed to the inner surface of the holder to align the needle along the axis;
   a substantially tubular shaped guard, wherein the guard is formed with a lumen for receiving the needle therein and is positioned in the lumen of the holder for reciprocal axial movement over the needle in a distal direction and in a proximal direction with an outer surface of the guard facing the inner surface of the holder;
   a cantilevered tab formed on the guard, wherein the tab is deflectable from the outer surface of the guard and into a stressed configuration for engagement with the distal abutment to prevent movement of the guard in a distal direction, and further wherein, in response to a proximal movement of the guard, the tab is released from its stressed configuration for movement into an unstressed configuration wherein the cantilevered tab is flush with the outer surface of the guard and clear of any interaction with the holder;
   a spring positioned in the lumen of the guard between the guard and the adapter to urge the guard in a distal direction along the axis to cover the needle when the cantilevered tab is in its unstressed configuration; and
   an extension limiter formed on the guard and engageable with the proximal abutment to prevent an uncovering of the needle by movement of the guard in a proximal direction.

2. A device as recited in claim 1 wherein the guard is sequentially moveable over the needle from an initial position wherein the cantilevered tab is urged against the first abutment and a distal portion of the needle extends from the guard, followed by a movement of the guard in the second direction to a retracted position wherein the cantilevered tab is released from the first abutment for transition to its unstressed configuration with further exposure of the needle, and a subsequent movement of the guard in the first direction to a final position wherein the guard covers the distal portion of the needle and the extension limiter is engaged with the proximal abutment to prevent an 10 uncovering of the distal portion of the needle.

3. A device as recited in claim 2 further comprising a cover engageable with the holder to cover the distal portion of the needle when the needle is in its initial position.

4. A device as recited in claim 3 further comprising a plurality of longitudinally oriented ribs mounted on the inner surface of the holder, the ribs individually extending from the inner surface of the holder with each rib having a detent for a snap engagement with the adapter.

5. A device as recited in claim 4 wherein the surface of the guard is formed with a pair of axially oriented ridges to create a groove for receiving one of the ribs therein to prevent rotation of the guard in the holder, and wherein the ridges urge against the holder to prevent movement in the first direction when the needle is in its final position.

6. A device as recited in claim 5 wherein the needle has a beveled first end and a second end, and wherein the adapter further comprises a pair of prongs extending therefrom to straddle the ribs to orient the needle and prevent a rotation of the adapter about the axis.

7. A device as recited in claim 1 wherein the needle is an aspiration needle.

8. A method for aspirating fluid which comprises the steps of:
   providing a device having a substantially tubular shaped holder defining a longitudinal axis and having an inner surface surrounding a lumen, a distal abutment formed on the inner surface of the holder, a proximal abutment formed on the inner surface of the holder, an adapter with the needle mounted thereon, the adapter being affixed to the inner surface of the holder to align the needle along the axis, a substantially tubular shaped guard, wherein the guard is formed with a lumen for receiving the needle therein and is positioned in the lumen of the holder for reciprocal axial movement over the needle in a distal direction and in a proximal direction with an outer surface of the guard facing the inner surface of the holder, a cantilevered tab formed on the guard, wherein the tab is deflectable from the outer surface of the guard and into a stressed configuration for engagement with the distal abutment to prevent movement of the guard in a distal direction, and further wherein, in response to a proximal movement of the guard, the tab is released from its stressed configuration for movement into an unstressed configuration wherein the cantilevered tab is flush with the outer surface of the guard and clear of any interaction with the holder, a spring positioned in the lumen of the guard between the guard and the adapter to urge the guard in a distal direction along the axis to cover the needle when the cantilevered tab is in its unstressed configuration and an extension limiter formed on the guard and engageable with the proximal abutment to prevent an uncovering of the needle by movement of the guard in a proximal direction;
   engaging the needle in fluid communication with the fluid source to move the guard from an initial position wherein the cantilevered tab is urged against the first abutment and a distal portion of the needle extends from the guard to a retracted position wherein the cantilevered tab is released from the first abutment for transition to its unstressed configuration with further exposure of the needle;
   withdrawing the needle from the fluid source to move the guard from the retracted position to a final position wherein the guard covers the distal portion of the needle and the extension limiter is engaged with the proximal abutment to prevent an uncovering of the distal portion of the needle; and discarding the device.

9. A method as recited in claim 8 further comprising the step of removing a cover from the holder to expose the distal portion of the needle when the needle is in its initial position.

10. A method as recited in claim 8 wherein the device further comprises a plurality of longitudinally oriented ribs mounted on the inner surface of the holder, the ribs individually extending from the inner surface of the holder with each rib having a detent for a snap engagement with the adapter, and wherein the surface of the guard is formed with a pair of axially oriented ridges to create a groove for receiving one of the ribs therein to prevent rotation of the guard in the holder, and further wherein the ridges urge against the holder to prevent movement in the first direction when the needle is in its final position.

11. A method as recited in claim 8 wherein the needle has a 20 beveled first end and a second end, and wherein the adapter further comprises a pair of prongs extending therefrom to straddle the ribs to orient the needle and prevent a rotation of the adapter about the axis.

* * * * *